(12) United States Patent
Clarke

(10) Patent No.: US 11,395,761 B2
(45) Date of Patent: Jul. 26, 2022

(54) IRIS SHIELD

(71) Applicant: Gerald Paul Clarke, Menasha, WI (US)

(72) Inventor: Gerald Paul Clarke, Menasha, WI (US)

(73) Assignee: ReaLens, Inc., Oshkosh, WI (US)

( * ) Notice: Subject to any disclaimer, the term of this patent is extended or adjusted under 35 U.S.C. 154(b) by 586 days.

(21) Appl. No.: 16/151,132

(22) Filed: Oct. 3, 2018

(65) Prior Publication Data

US 2020/0107954 A1 Apr. 9, 2020

(51) Int. Cl.
*A61F 9/00* (2006.01)
*A61F 9/007* (2006.01)
*A61B 17/02* (2006.01)

(52) U.S. Cl.
CPC ........ *A61F 9/0017* (2013.01); *A61B 17/0231* (2013.01); *A61F 9/007* (2013.01); *A61F 9/00736* (2013.01); *A61F 2250/0059* (2013.01)

(58) Field of Classification Search
CPC ............ A61B 17/0231; A61B 17/0293; A61B 17/0206; A61F 9/0017; A61F 2009/00876; A61F 9/007; A61F 9/00736; A61F 2250/0059; A61F 9/0008
See application file for complete search history.

(56) References Cited

U.S. PATENT DOCUMENTS

| | | | |
|---|---|---|---|
| 1,506,186 | A | 8/1924 | Owen et al. |
| 2,761,457 | A | 9/1956 | Wood |
| 3,490,455 | A | 1/1970 | Illig |
| 3,975,779 | A | 8/1976 | Richards et al. |

(Continued)

FOREIGN PATENT DOCUMENTS

| | | |
|---|---|---|
| EP | 2 903 577 B1 | 2/2015 |
| KR | 20160020855 | 2/2016 |

(Continued)

OTHER PUBLICATIONS

Extended European Search Report for EP Application No. 18215957.4-1124, dated Sep. 18, 2019, 8 pages.

(Continued)

*Primary Examiner* — Sarah W Aleman
(74) *Attorney, Agent, or Firm* — Stephen C. Jensen; Davis & Kuelthau

(57) ABSTRACT

Apparatus and methods, and uses of apparatus, for preventing prolapse of iris tissue, through a surgical opening in the eye during eye surgery. Early in the surgery, one or more surgical openings are made in the eye, and a flexible biocompatible iris shield is inserted, through a such opening, into the anterior chamber and placed in a position whereby the iris shield overlies the iris anteriorly, adjacent each surgical opening and is positioned between the iris and any surgical openings. If/when the pressure inside the anterior chamber increases during surgery, any anterior movement of the iris toward the cornea or sclera in response to such pressure, moves the iris shield in an anterior direction, such that the iris shield remains between the iris and the surgical opening. Thus, the iris shield blocks the surgical opening and prevents movement of eye material, e.g. iris tissue, to and through the surgical opening.

21 Claims, 10 Drawing Sheets

(56) References Cited

U.S. PATENT DOCUMENTS

| | | | |
|---|---|---|---|
| 3,991,426 A | 11/1976 | Flom et al. | |
| 4,203,168 A | 5/1980 | Rainin et al. | |
| 4,387,706 A | 6/1983 | Glass | |
| 4,782,820 A * | 11/1988 | Woods | A61F 2/14 600/208 |
| 4,991,567 A | 2/1991 | McCuen, II et al. | |
| 5,021,057 A | 6/1991 | Byrne, Jr. | |
| 5,163,419 A | 11/1992 | Goldman | |
| 5,174,279 A | 12/1992 | Cobo et al. | |
| 5,267,553 A | 12/1993 | Graether | |
| 5,299,564 A | 4/1994 | Sabatino | |
| 5,318,011 A | 6/1994 | Federman et al. | |
| 5,322,054 A | 6/1994 | Graether | |
| 5,374,272 A * | 12/1994 | Arpa | A61B 17/0231 600/236 |
| 5,427,088 A | 6/1995 | Graether | |
| 5,441,045 A | 8/1995 | Federman et al. | |
| 5,634,884 A | 6/1997 | Graether | |
| 5,824,086 A | 10/1998 | Silvestrini | |
| 5,951,565 A | 9/1999 | Freeman | |
| 6,068,643 A | 5/2000 | Milverton | |
| 6,228,093 B1 | 5/2001 | Tomalla | |
| 6,231,583 B1 | 5/2001 | Lee | |
| 6,332,866 B1 | 12/2001 | Grieshaber et al. | |
| 6,620,098 B1 | 9/2003 | Milverton | |
| 8,323,296 B2 | 12/2012 | Malyugin | |
| 8,496,583 B1 | 7/2013 | Reynard | |
| 8,900,136 B2 | 12/2014 | Cote et al. | |
| 9,089,397 B2 | 7/2015 | Clarke | |
| 9,504,459 B1 | 11/2016 | Nallakrishnan | |
| 9,763,653 B2 | 9/2017 | Malyugin et al. | |
| 9,918,710 B2 | 3/2018 | Malyugin et al. | |
| 9,980,852 B2 | 5/2018 | Malyugin et al. | |
| 2003/0092970 A1 * | 5/2003 | Lee | A61B 17/0231 600/236 |
| 2006/0235428 A1 | 10/2006 | Silvestrini | |
| 2008/0243139 A1 | 10/2008 | Dusek | |
| 2008/0269564 A1 * | 10/2008 | Gelnett | A61B 17/02 600/201 |
| 2008/0269888 A1 | 10/2008 | Malyugin | |
| 2008/0275461 A1 | 11/2008 | Nallakrishnan | |
| 2010/0076270 A1 | 3/2010 | Merriam | |
| 2012/0136322 A1 | 5/2012 | Alster et al. | |
| 2012/0289786 A1 | 11/2012 | Dusek | |
| 2013/0053860 A1 | 2/2013 | Malyugin | |
| 2013/0096386 A1 | 4/2013 | Christensen et al. | |
| 2013/0131458 A1 | 5/2013 | Malyugin et al. | |
| 2013/0267988 A1 | 10/2013 | Sussman et al. | |
| 2013/0331939 A1 | 12/2013 | Stevens | |
| 2014/0090653 A1 * | 4/2014 | Clarke | A61F 9/04 128/858 |
| 2014/0221759 A1 | 8/2014 | Mackool et al. | |
| 2014/0316520 A1 * | 10/2014 | Barsam | A61F 2/1694 623/4.1 |
| 2014/0378773 A1 | 12/2014 | Dykes | |
| 2015/0164685 A1 | 6/2015 | Bhattacharjee | |
| 2015/0265269 A1 | 9/2015 | Malyugin et al. | |
| 2015/0366704 A1 * | 12/2015 | Eippert | A61F 9/007 600/236 |
| 2017/0312126 A1 | 11/2017 | Malyugin et al. | |

FOREIGN PATENT DOCUMENTS

| | | |
|---|---|---|
| WO | WO 2008/115454 | 9/2008 |
| WO | WO 2008/115455 | 9/2008 |

OTHER PUBLICATIONS

Uday Devgan, Management of iris prolapsed in cataract surgery, The technique of equalizing pressure gradients, Ocular Surgery News, Oct. 15, 2006, Article printed Sep. 6, 2012, 4 pages, Ocular Surgery News U.S. Edition.

* cited by examiner

IRIS SHIELD

BACKGROUND OF THE INVENTION

This invention relates to ophthalmic surgeries performed on the eye. The invention relates specifically to such surgeries where an increased pressure is developed inside the eye enclosure. Such surgeries include, for example and without limitation, cataract surgery, vitrectomy, glaucoma procedures, and other procedures undertaken behind the iris.

During such surgeries, one or more surgical openings are created in the anterior portion of the eye for the purpose of inserting, into the eye, various surgical instruments, as well as fluids and other assisting items which are used in the surgical procedure or which are temporarily inserted into the eye during the procedure, or which are inserted for the purpose of leaving such item in the eye as part of the surgical procedure. Such surgical openings are commonly created adjacent, and anterior of, the iris, generally adjacent the outer perimeter of the iris, optionally in the sclera.

During such surgical procedures, it is common to add one or more fluids to the anterior chamber of the eye, and it is common that at least some of such added fluid is positioned behind the iris. The addition of such fluid can cause an increase in the fluid pressure inside the eye.

In addition, the pupil may not dilate sufficiently by itself to facilitate the surgical procedure, such that additional devices may be inserted into the anterior chamber to manually dilate the pupil in order to safely remove a cataract or to perform other procedures behind the iris.

For example, during cataract surgery, one or more surgical openings may be made adjacent the outer perimeter of, and in front of, the iris. One or more instruments are inserted through the surgical openings, in front of the iris, and manipulated inside the anterior chamber, along with administration of suitable fluids inside the anterior chamber, in removing the original natural lens, and inserting a replacement intraocular lens in its place.

During the surgery, the patient may tense the eyelids, which also raises the pressure inside the eye.

Elements of the iris tissue are relatively thin, and are loosely connected to each other. The iris, as a whole, is quite mobile. The iris responds to any such increase in pressure by moving away from the area of relatively greater pressure toward an area of relatively lower pressure. The ambient atmosphere outside the eye is such an area of lower pressure.

In addition, the strength of the iris tissue can vary from patient to patient, depending on a number of health-related factors, and/or life style factors, including any drugs, such as sympathetic blockers, which the patient may be using. The pupil dilation varies between patients for the same reasons The surgical opening(s) are made through relatively soft and extensible tissue. To the extent any area of a surgical opening is not fully occupied by an instrument or other article, or to the extent the surgical opening is enlarged slightly by the internal pressure inside the anterior chamber, such as by stretching the tissue surrounding the surgical opening, the unoccupied or enlarged opening can provide a path for the iris tissue to move toward that area of lower pressure outside the eye. Any such movement of the iris tissue outside its normal zone of movement creates abnormal stresses on the iris tissue, and can be damaging to the iris tissue.

The result of such abnormal movement of the iris tissue may be the protrusion of iris tissue, commonly referred to as prolapse, through the surgical opening to the area of lower pressure outside the eye. Such prolapse of iris tissue through the surgical opening creates abnormal stresses in the iris tissue and can, in some cases, result in tearing of the iris tissue.

FIG. 1 shows an example of a generally healthy human eye 2 before a surgical procedure has been initiated. There are no openings in the outer tissue adjacent the anterior chamber. There is no path for the iris tissue to exit/prolapse the eye enclosure.

FIG. 2 shows the same eye as in FIG. 1, but illustrating such prolapse. FIG. 2 illustrates a surgical opening 3 created through the cornea 4 or sclera 5 adjacent the outer edge of the iris 6. As a result of increased pressure inside the anterior chamber 7, for example during a surgical procedure, the iris has begun to prolapse through the surgical opening and thus a prolapsed portion 8 of the iris extends outside the eye.

It is desirable to prevent any prolapse, which can damage and/or tear the iris tissue. Even where the prolapsed tissue can be drawn back inside the eye enclosure through the surgical opening, such trauma to the eye can result in the patient experiencing pain during the surgery and the patient may experience excessive glare post-surgery.

It is also desirable to maintain adequate pupil dilation throughout the surgery.

Thus, the problem to be solved by the invention is to maintain adequate pupil dilation while addressing prolapse, by preventing the occurrence of prolapse.

A conventional treatment for iris prolapse is to watch for prolapse, and to react to such prolapse when prolapse is observed during the surgical procedure. The conventional reaction to prolapse, once the prolapse is observed, is to maintain the increased pressure in the anterior chamber behind the iris, and to increase the pressure inside the anterior chamber in front of the iris. Such increase in pressure in front of the iris apparently urges the iris tissue which remains inside the eye envelope to move rearwardly inside the eye enclosure, thus drawing the prolapsed tissue back through the surgical opening and inside the eye.

Another conventional treatment is to depress the iris and the intraocular lens inside the eye when the iris prolapses.

Still another conventional treatment is to place a viscoelastic plug in any surgical opening which is not needed immediately, for the period when the pressure is to be increased in the anterior chamber, and then to remove the viscoelastic plug as part of completing the surgical procedure.

Any tissue which may have been torn in the process of a prolapse may be permanently lost. In addition, any iris tissue which has been exposed to ambient atmosphere in the meantime, has also been exposed to any contaminants in the atmosphere, including any pathogenic bacteria, viruses, and the like with which the prolapsed tissue may have come into contact in the atmosphere. So allowing the prolapse to occur, and then responding to that occurrence, entails additional risk of contamination and/or tissue tearing, including the risk of corresponding complications developing as a result of the surgery.

Thus it would be desirable to provide a proactive method for preventing the occurrence of iris prolapse while maintaining adequate pupil dilation.

It would further be desirable to prevent the iris tissue from becoming exposed to the ambient environment outside the eye enclosure.

It would be further desirable to prevent the stress and potential for tearing of iris tissue as a result of increased pressure inside the eye enclosure while performing ophthalmic surgery.

It would be desirable to provide a device which would immobilize the inner edge of the iris and maintain dilation of the iris for the duration of surgery, thereby assisting visualization of the deeper contents (e.g. lens) of the eye during surgery.

It would further be desirable to avoid inserting small temporary plugs into the surgical opening, lest such small items become fragmented, or be inadvertently left inside the anterior chamber at the end of the surgery.

These and other needs are alleviated, or at least attenuated, by the novel apparatus, methods, and uses of the invention.

SUMMARY OF THE INVENTION

This invention provides apparatus and methods, and uses of such apparatus, for preventing prolapse of iris tissue or any other eye tissue, through a surgical opening in the cornea or sclera, out of the eye during an ophthalmic surgical procedure. At an early stage of the surgical procedure, one or more surgical openings are made in the anterior portion of the eye, and a suitably flexible, or otherwise configurable, biocompatible polymeric iris shield is inserted through a such surgical opening into the anterior chamber of the eye and placed in a position whereby the iris shield overlies the iris adjacent each of the surgical openings, and is remote/displaced from the cornea. The iris shield is thus positioned between the iris tissue and any surgical openings. This also has the effect of dilating the pupil so that surgical exposure to the lens and deeper tissues is improved. If/when the pressure inside the anterior chamber increases during the surgical procedure, any anterior movement of the iris toward the cornea or sclera, namely toward any such surgical opening in response to such pressure, also lifts the iris shield in an anterior direction, such that the iris shield remains between the iris and the respective surgical openings. Thus, the iris shield blocks the surgical opening and prevents movement of eye material, e.g. iris tissue, to and through the surgical opening. Namely, the iris shield closes off access to the surgical opening from inside the eye. The surgical opening can, of course, still be accessed by surgical tools and materials from outside the eye by inserting such articles through the surgical opening and pushing such articles past the flexible iris shield which is overlying the iris.

In a first family of embodiments, the invention comprehends an iris shield adapted and configured to be inserted through a surgical opening and into an anterior chamber of an eye during a surgery, such anterior chamber having a circumference, such eye comprising an iris in such anterior chamber, such iris having an outer edge, an inner edge, and an iris width between the iris outer edge and the iris inner edge, the iris shield comprising a flexible biocompatible polymeric sheet, the sheet, and correspondingly the iris shield, having an anterior side for facing forwardly in the eye, and a posterior side for facing rearwardly in the eye, an inner edge extremity and an outer edge extremity, and a width (W1) between the inner edge extremity and the outer edge extremity; and a single retention flange extending from the biocompatible polymeric sheet adjacent the inner edge extremity, the single retention flange being disposed on the posterior side of the biocompatible polymeric sheet, the iris shield being suitable for being temporarily placed on the iris in the eye during a surgery, and to thereby overlie the iris adjacent the surgical opening such that, when pressure inside the eye urges tissue of the iris toward the surgical opening during the surgery, the iris shield interferes with the iris tissue reaching the surgical opening, the iris shield being adapted and configured to being removed from the eye prior to completion of the surgery.

In some embodiments, the single retention flange extends along at least 60 degrees, optionally along at least about 90 degrees, optionally along at least about 150 degrees, optionally along at least about 235 degrees, optionally along at least about 305 degrees, optionally along at least about 335 degrees, of the circumference of the anterior chamber. In some embodiments, the extent of the flange and polymeric sheet may extend only to 270 degrees to accommodate smaller eyes.

In some embodiments, the biocompatible polymeric sheet has first and second ends, and first and second manipulation apertures proximate the first and second ends of the biocompatible polymeric sheet, the manipulation apertures extending through the biocompatible polymeric sheet from the anterior side to the posterior side, at least one eyelet substantially surrounding at least one of the first and second manipulation apertures, a given eyelet having a third side corresponding to the anterior side of the biocompatible sheet, and a fourth side corresponding to the posterior side of the biocompatible polymeric sheet, the at least one eyelet having a first thickness between the third side and the fourth side, the biocompatible polymeric sheet having a main body portion extending generally from the at least one eyelet, the main body portion having a second thickness less than the first thickness.

In some embodiments, the biocompatible polymeric sheet has first and second ends, the iris shield extending along at least 360 degrees of the circumference of the anterior chamber when so inserted into the eye and positioned to protect such iris during the surgery.

In some embodiments, the biocompatible polymeric sheet has first and second ends, the iris shield extending along up to about 410 degrees of the circumference of the anterior chamber between the first and second ends when so inserted into the eye and positioned to protect the iris during the surgery, whereby the first and second ends of the iris shield overlap each other when the iris shield extends more than 360 degrees.

In some embodiments, the biocompatible polymeric sheet has first and second ends, the iris shield extending along greater than 360 degrees of the circumference of the anterior chamber between the first and second ends when so inserted into the eye and positioned to protect the iris during the surgery, wherein the first and second ends of the iris shield overlap each other, the at least one eyelet substantially surrounding the first manipulation aperture, and wherein the first and second sides of the iris shield at the second aperture comprise straight line extensions of respective anterior side and posterior side of the main body portion.

In a second family of embodiments, the invention comprehends an iris shield adapted and configured to be inserted through a surgical opening and into an anterior chamber of a living eye during a surgery, the anterior chamber having a circumference, an iris being disposed in, and extending about the circumference of, the anterior chamber, the iris having an outer edge, an inner edge, and an iris width between the iris outer edge and the iris inner edge, the iris shield comprising a flexible biocompatible polymeric sheet, the sheet, and correspondingly the iris shield, having an anterior side for facing frontwardly in the eye, and a posterior side for facing rearwardly in the eye, an inner edge extremity and an outer edge extremity, and a width (W1) between the inner edge extremity and the outer edge extremity; and a retention flange extending from the biocompatible polymeric sheet adjacent the inner edge extremity, the retention flange being disposed on the posterior side of the biocompatible polymeric sheet and extending along at least 60 degrees of the circumference of the anterior chamber adjacent the surgical opening when so inserted into the eye during the surgery, the iris shield being suitable for being temporarily placed on the iris in the eye adjacent the surgical opening, thereby to overlie a substantial portion of a circumference of the iris such that, when pressure inside the eye urges tissue of the iris toward the surgical opening during the surgery, the iris shield interferes with the iris tissue reaching the surgical opening, the iris shield being adapted and configured to being removed from the eye prior to completion of the surgery.

In some embodiments, the iris shield extends along at least 90 degrees, optionally along at least 210 degrees, optionally along at least 270 degrees, of the circumference of the iris when so inserted into the eye during the surgery.

In some embodiments, the iris shield has first and second ends, and the iris shield extends greater than 360 degrees about the circumference of the iris when so inserted into the eye and positioned to protect the iris during the surgery whereby the first and second ends of the iris shield overlap each other.

In some embodiments, the iris shield has first and second ends, and the iris shield extends along up to about 410 degrees of a circumference of the iris when so inserted into the eye and positioned to protect the iris during such surgery, whereby the first and second ends of the iris shield overlap each other.

In a third family of embodiments, the invention comprehends an iris shield adapted and configured to be inserted through a surgical opening and into an anterior chamber of a living eye during a surgery, the anterior chamber having a circumference, an iris being disposed in, and extending about the circumference of, the anterior chamber, the iris having an outer edge, an inner edge, and an iris width between the iris outer edge and the iris inner edge, the iris shield comprising a flexible biocompatible polymeric sheet, the sheet, and correspondingly the iris shield, having first and second ends, an anterior side for facing frontwardly in the eye, and a posterior side for facing rearwardly in the eye, an inner edge extremity and an outer edge extremity, and a width (W1) between the inner edge extremity and the outer edge extremity; and the iris shield extending along at least 360 degrees of the circumference of the anterior chamber between the first and second ends when so inserted into the eye and positioned to protect the iris during such surgery, the iris shield being suitable for being temporarily placed on the iris, and at least the inner edge extremity and central portions of the width of the iris shield, being spaced from the cornea of the eye when the eye experiences normal eye pressures in the anterior chamber, thereby to overlie the iris such that, when pressure inside the eye urges tissue of the iris toward the surgical opening during the surgery, the iris shield interferes with the iris tissue reaching the surgical opening, the iris shield being adapted and configured to being removed from the eye prior to completion of the surgery.

In some embodiments, a single retention flange extends from the biocompatible polymeric sheet adjacent the inner edge extremity, the single retention flange being disposed on the posterior side of the biocompatible polymeric sheet, and optionally extending along at least 150 degrees of the circumference of the anterior chamber.

In some embodiments, the single retention flange extends along at least about 305 degrees of the circumference of the anterior chamber, and the first and second ends of the iris shield overlap each other when the iris shield extends more than 360 degrees about the circumference of the anterior chamber.

In a fourth family of embodiments, the invention comprehends an iris shield for insertion through a surgical opening and into an anterior chamber of an eye during a surgery, the eye comprising an iris in the anterior chamber, the iris having an outer edge, an inner edge, and an iris width between the iris outer edge and the iris inner edge, the iris shield comprising a flexible biocompatible polymeric sheet, the sheet, and correspondingly the iris shield, having first and second ends, an anterior side for facing forwardly in the eye, a posterior side for facing rearwardly in the eye, an inner edge extremity and an outer edge extremity, and a width (W1) between the inner edge extremity and the outer edge extremity; first and second manipulation apertures proximate the first and second ends of the biocompatible polymeric sheet, the manipulation apertures extending through the biocompatible polymeric sheet between the anterior side and the posterior side; and at least one eyelet substantially surrounding at least one of the first and second manipulation apertures, a given eyelet having a third side corresponding to the anterior side of the biocompatible polymeric sheet, and a fourth side corresponding to the posterior side of the biocompatible polymeric sheet, the at least one eyelet having a first thickness between the third side and the fourth side, the biocompatible polymeric sheet having a main body portion extending generally from the at least one eyelet, the main body portion having a second thickness less than the first thickness, the iris shield being suitable for being temporarily placed on the iris in the eye and to thereby overlie a substantial portion of the iris adjacent the surgical opening such that, when pressure inside the eye urges tissue of the iris toward the surgical opening during the surgery, the iris shield interferes with the iris tissue reaching the surgical opening, the iris shield being adapted and configured to be removed from the eye prior to completion of the surgery.

In some embodiments, the magnitude of the first thickness is about 1.3 times to about 2.5 times the magnitude of the second thickness.

In some embodiments, the fourth side of the eyelet comprises a straight line extension of the main body portion of the iris shield.

In a fifth family of embodiments, the invention comprehends a method of treating a living eye during an ophthalmic surgery, the eye having an anterior chamber, and an iris in the anterior chamber, the iris having an outer edge, an inner edge, an iris width between the iris outer edge and the iris inner edge, the anterior chamber having an outer circumference, the method comprising creating a single surgical opening into the anterior chamber of the eye; inserting an iris shield into the anterior chamber through the surgical opening, the iris comprising a flexible biocompatible polymeric sheet, the sheet, and correspondingly the iris shield, having an anterior side facing frontwardly in the eye, and a posterior side facing rearwardly in the eye, an inner edge extremity and an outer edge extremity, and a width (W1) between the inner edge extremity and the outer edge extremity, the iris shield having first and second ends and extending along at least 350 degrees of the circumference of the anterior chamber, and overlapping each other when the iris shield extends more than 360 degrees; positioning the iris shield on the iris with the iris shield overlying a substantial portion of the width of the iris adjacent the surgical opening such that, when pressure inside the eye urges tissue of the iris toward the surgical opening, the iris shield interferes with the iris tissue reaching the surgical opening and prolapsing out of the eye; performing at least one surgical procedure while the iris shield is positioned on the iris, including positioned adjacent the surgical opening; and as part of completing the ophthalmic surgery, removing the iris shield from the eye.

In a sixth family of embodiments, the invention comprehends a method of treating a living eye during an ophthalmic surgery, the eye having an anterior chamber, and an iris in the anterior chamber, the iris having an outer edge, an inner edge, an iris width between the iris outer edge and the iris inner edge, the anterior chamber having an outer circumference, the method comprising creating at least one surgical opening into the anterior chamber of the eye; inserting an iris shield into the anterior chamber through the surgical opening, the iris shield comprising a configurable, optionally flexible, biocompatible polymeric sheet, the sheet, and correspondingly the iris shield, having an anterior side facing frontwardly in the eye, and a posterior side facing rearwardly in the eye, an inner edge extremity and an outer edge extremity, and a width (W1) between the inner edge extremity and the outer edge extremity, the iris shield extending along greater than 360 degrees of the outer circumference of the anterior chamber of the eye whereby the first and second ends overlap each other; positioning the iris shield on the iris, with the iris shield overlying a substantial portion of the width of the iris such that, when pressure inside the eye urges tissue of the iris toward the surgical opening, the iris shield interferes with the iris tissue reaching the surgical opening and prolapsing out of the eye; performing at least one surgical procedure while the iris shield is positioned on the iris, including positioned adjacent the surgical opening; and as part of completing the ophthalmic surgery, removing the iris shield from the eye.

In some embodiments, the iris shield further comprises a retention flange extending from the biocompatible polymeric sheet adjacent the inner edge extremity, the flange being disposed on the posterior side of the sheet and extending along at least 150 degrees, and up to about 335 degrees, of the circumference of the anterior chamber.

In a seventh family of embodiments, the invention comprehends use of an iris shield in an eye during a surgery, the eye having an anterior chamber, the anterior chamber having an outer circumference, the eye further comprising a pupil, a cornea, and an iris in the anterior chamber, the iris having an outer edge, an inner edge, and an iris width between the iris outer edge and the iris inner edge, the iris shield comprising a flexible biocompatible polymeric sheet, the sheet, and correspondingly the iris shield, having an anterior side for facing forwardly in the eye, and a posterior side for facing rearwardly in the eye, an inner edge extremity and an outer edge extremity, and a width (W1) between the inner edge extremity and the outer edge extremity, and a single retention flange extending from the biocompatible polymeric sheet adjacent the inner edge extremity, the single retention flange being disposed on the posterior side of the biocompatible polymeric sheet, the use comprising inserting the iris shield through a surgical opening in the eye during the surgery, with the iris shield being disposed on the iris and overlying a substantial portion of the width of the iris adjacent the surgical opening so as to prevent iris tissue from circumventing the iris shield such that, when pressure inside the eye urges tissue of the iris toward the surgical opening, the iris shield interferes with the iris tissue flowing out the surgical opening, the iris shield being adapted and configured to be removed from the eye prior to completion of the surgery.

In some embodiments, the single retention flange extends along at least 60 degrees, optionally at least 235 degrees, optionally at least 305 degrees, of the circumference of the anterior chamber.

In some embodiments, the biocompatible polymeric sheet has first and second ends, further comprising first and second manipulation apertures proximate the first and second ends of the biocompatible polymeric sheet, the manipulation apertures extending through the biocompatible polymeric sheet, from the anterior side to the posterior side, at least one eyelet substantially surrounding at least one of the first and second manipulation apertures, a given eyelet having a third side corresponding to the anterior side of the biocompatible sheet, and a fourth side corresponding to the posterior side of the biocompatible polymeric sheet, the at least one eyelet having a first thickness between the third side and the fourth side, the biocompatible polymeric sheet having a main body portion extending generally from the at least one eyelet, the main body portion having a second thickness less than the first thickness.

In some embodiments, the fourth side of the eyelet comprises a straight line extension of the main body portion of the iris shield.

In some embodiments, the biocompatible polymeric sheet has first and second ends, and the iris shield extends at least about 350 degrees up to about 410 degrees along the outer circumference of the anterior chamber, including the first and second ends overlapping each other when the iris shield extends more than 360 degrees.

In some embodiments, the retention flange extends about 295 degrees to about 355 degrees along the circumference of the anterior chamber.

In an eighth family of embodiments, the invention comprehends use of an iris shield in an eye during a surgery, the eye having an anterior chamber, the anterior chamber having an outer circumference, the eye further comprising a pupil, a cornea, and an iris in the anterior chamber, the iris having an outer edge, an inner edge, and an iris width between the iris outer edge and the iris inner edge, the iris shield comprising a flexible biocompatible polymeric sheet, the sheet, and correspondingly the iris shield, having an anterior side for facing forwardly in the eye, and a posterior side for facing rearwardly in the eye, an inner edge extremity and an outer edge extremity, and a width (W1) between the inner edge extremity and the outer edge extremity, a retention flange extending from the biocompatible polymeric sheet adjacent the inner edge extremity, the retention flange being disposed on the posterior side of the biocompatible polymeric sheet and extending along at least 60 degrees of the outer circumference of the anterior chamber when so inserted into the eye and positioned to protect the iris during the surgery, the use comprising inserting the iris shield through a surgical opening in the eye during the surgery, with the iris shield being disposed on the iris and overlying a substantial portion of the width of the iris adjacent the surgical opening so as to prevent iris tissue from circumventing the iris shield such that, when pressure inside the eye urges tissue of the iris toward the surgical opening, the iris shield interferes with the iris tissue flowing out the surgical opening, the iris shield being adapted and configured to be removed from the eye prior to completion of the surgery.

In some embodiments, the retention flange extends along at least 90 degrees, optionally at least 150 degrees, optionally at least 235 degrees, optionally at least 305 degrees, of the circumference of the anterior chamber when inserted into the eye, and positioned to protect the iris, during the surgery.

In some embodiments, the iris shield comprises first and second ends and extends along at least 360 degrees of the circumference of the anterior chamber when so inserted into the eye during the surgery.

In some embodiments, the biocompatible polymeric sheet has first and second ends, further comprising first and second manipulation apertures proximate the first and second ends of the biocompatible polymeric sheet, the manipulation apertures extending through the biocompatible polymeric sheet, from the anterior side to the posterior side, at least one eyelet substantially surrounding at least one of the first and second manipulation apertures, a given eyelet having a third side corresponding to the anterior side of the biocompatible sheet, and a fourth side corresponding to the posterior side of the biocompatible polymeric sheet, the at least one eyelet having a first thickness between the third side and the fourth side, the biocompatible polymeric sheet having a main body portion extending generally from the at least one eyelet, the main body portion having a second thickness less than the first thickness.

In some embodiments, the fourth side of the eyelet comprises a straight line extension of the main body portion of the iris shield.

In a ninth family of embodiments, the invention comprehends use of an iris shield in an eye during a surgery, the eye having an anterior chamber, the anterior chamber having an outer circumference, the eye further comprising a pupil, a cornea, and an iris, the iris having an outer edge, an inner edge, and an iris width between the iris outer edge and the iris inner edge, the iris shield comprising a flexible biocompatible polymeric sheet, the sheet, and correspondingly the iris shield, having first and second ends, an anterior side for facing forwardly in the eye, and a posterior side for facing rearwardly in the eye, an inner edge extremity and an outer edge extremity, and a width (W1) between the inner edge extremity and the outer edge extremity, first and second manipulation apertures proximate the first and second ends of the biocompatible polymeric sheet, the manipulation apertures extending through the biocompatible polymeric sheet between the anterior side and the posterior side, at least one eyelet substantially surrounding at least one of the first and second manipulation apertures, a given eyelet having a third side corresponding to the anterior side of the biocompatible polymeric sheet, and a fourth side corresponding to the posterior side of the biocompatible polymeric sheet, the at least one eyelet having a first thickness between the third side and the fourth side, the biocompatible polymeric sheet having a main body portion extending generally from the at least one eyelet, the main body portion having a second thickness less than the first thickness, the use comprising inserting the iris shield through a surgical opening in the eye during the surgery, with the iris shield being disposed on the iris and overlying a substantial portion of the width of the iris adjacent the surgical opening so as to prevent iris tissue from circumventing the iris shield such that, when pressure inside the eye urges tissue of the iris toward the surgical opening, the iris shield interferes with the iris tissue flowing out the surgical opening, the iris shield being adapted and configured to be removed from the eye prior to completion of the surgery.

In some embodiments, the iris shield extends along about 350 degrees to about 410 degrees of the circumference of the anterior chamber, including the first and second ends overlapping each other when the iris shield extends more than 360 degrees.

In some embodiments, use of the iris shield further comprises a retention flange extending from the biocompatible polymeric sheet adjacent the inner edge extremity, the retention flange being disposed on the posterior side of the biocompatible polymeric sheet and extending along at least 90 degrees of the circumference of the anterior chamber when inserted into the eye and positioned to protect the iris during the surgery.

In some embodiments, the use further comprises a retention flange extending from the biocompatible polymeric sheet adjacent the inner edge extremity, the retention flange being disposed on the posterior side of the biocompatible polymeric sheet and extending along at least about 350 degrees, up to about 410 degrees, of the circumference of the anterior chamber when inserted into the eye, and positioned to protect the iris, during surgery, including the first and second ends overlapping each other when the iris shield extends more than 360 degrees.

In some embodiments, two or three segments of the polymeric sheet may be connected to each other by hinges, with the hinges being located in one or more of the eyelets, such as in the single center eyelet or in the two eyelets on either side of the center eyelet. The hinges enable the iris shield to flex within the pupillary space, thereby to adjust to different size pupils.

These and other features and advantages of this invention are described in, or are apparent from, the following detailed description of various exemplary embodiments of the apparatus and methods, and uses, according to this invention.

BRIEF DESCRIPTION OF THE DRAWINGS

A more complete understanding of the present invention and the attendant features and advantages thereof may be had by reference to the following detailed description when considered in combination with the accompanying drawings wherein various figures depict certain embodiments of the various elements, and methods of use, of iris shields of the invention.

Figure 1:
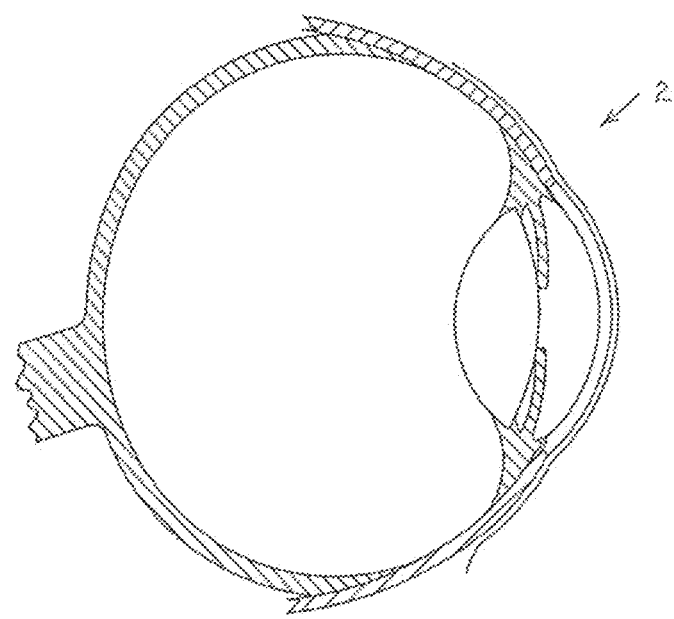
FIG. 1 shows a relatively healthy human eye prior to any performance of ophthalmic surgery.
Figure 2:
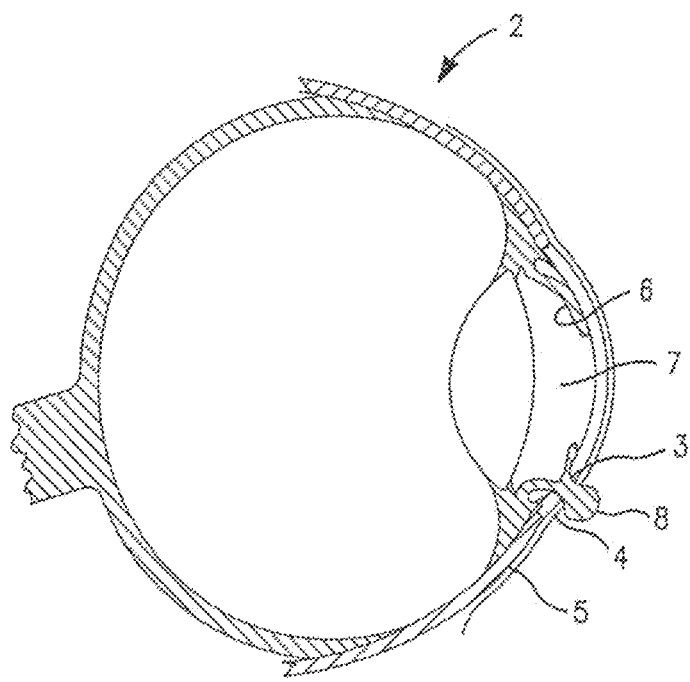
FIG. 2 shows the eye of FIG. 1 with a prolapsed iris after a surgical opening has been created in the eye enclosure and pressure has been increased in the anterior chamber behind the iris.

The invention is not limited in its application to the details of construction, or to the arrangement of the components set forth in the following description or illustrated in the drawings. The invention is capable of other embodiments or of being practiced or carried out in various other ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

In the invention, a sheet-shaped shield of slightly stiff, biocompatible polymeric material is inserted into the anterior chamber of the eye, through a peripheral corneal or sclera surgical opening, and placed on the iris inside the eye to prevent prolapse of iris tissue to the outside of the eye by adding an intervening blocking support between the iris tissue and the surgical opening, and also enabling the attending physician to engage the inner edge of the iris to, as an additional benefit, assist in dilating the iris and/or preventing constriction of the iris over the pupil.

In use, an iris shield of the invention is first drawn into a tubular injector having a plunger inside the tube. With the iris shield inside the injector tube, and after a surgical opening has been made in the eye to be treated, frontwardly of the iris in the eye, the injector is inserted into the anterior chamber of the eye through the surgical opening and the plunger is gently pushed through the injector tube, thereby to expel the iris shield into the anterior chamber of the eye being treated. The injector is then removed from the eye, leaving the iris shield inside the anterior chamber of the eye. The attending physician then uses conventional tools to manipulate the iris shield into a desired position overlying the iris and optionally engaging and temporarily immobilizing the inner edge of the iris.

Figure 3:
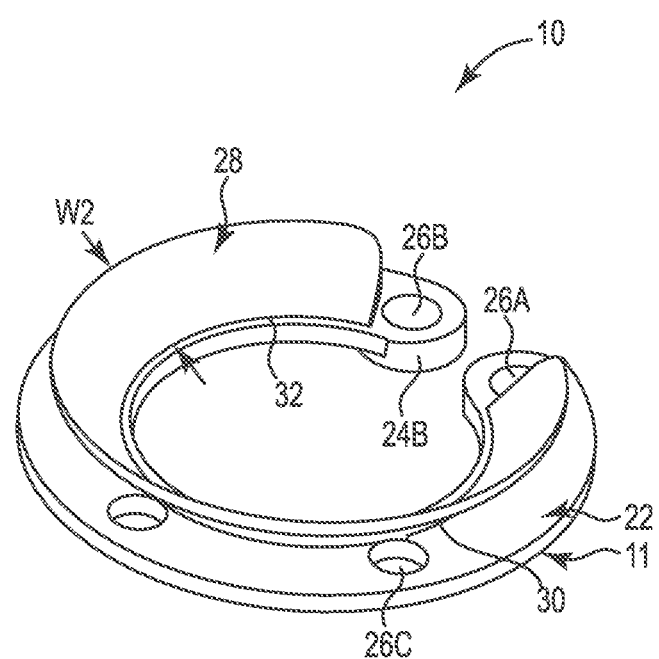
FIG. 3 is a pictorial representation of the posterior side of a first embodiment of iris shields of the invention, the iris shield having a single retention flange extending substantially the full length of the main body of the iris shield.
Figure 4:
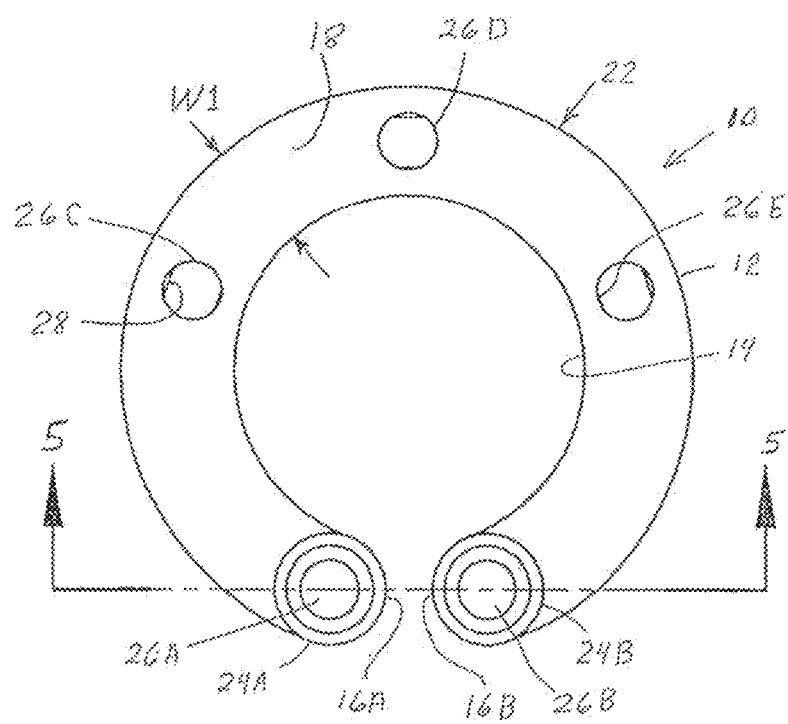
FIG. 4 is a plan view of the anterior side of the iris shield of FIG. 3.
Figure 5:
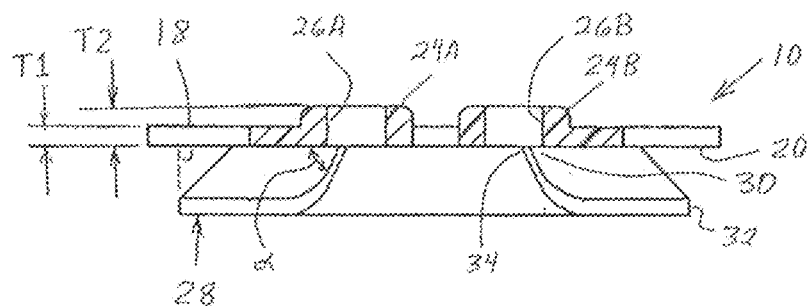
FIG. 5 is a cross-section of the iris shield of FIGS. 3 and 4, taken at 5-5 of FIG. 4.

Referring to the drawings, FIGS. 3-5 illustrate a first embodiment of iris shields of the invention. FIG. 3 shows a curved, generally circular-shaped, iris shield 10 which extends about 350 degrees about the circumference of an imaginary circle. FIG. 4 shows a plan view of the same iris shield, looking at an anterior side of the iris shield. FIG. 5 is a cross-section of the iris shield of FIG. 4, taken at 5-5 of FIG. 4.

Iris shield 10 is made of a flexible surgical-grade polymer. The iris shield shown in FIGS. 3-5 generally conforms, along its length, to the substantially circular outline of the iris of a human eye. Iris shield 10 has a generally constant-thickness base sheet 11, including the outer edge extremity 12, the inner edge extremity 14, and a width "W1" between the inner and outer edge extremities extending from a first end 16A of the iris shield to a second end 16B of the iris shield. The first and second ends 16A, 168 extend in generally circular arcs between the outer edge extremity 12 and the inner edge extremity 14 as the ends connect the inner and outer edge extremities to each other.

Iris shield 10 has an anterior side 18 which faces frontwardly in the eye and a posterior side 20 which faces rearwardly in the eye. Main body 22 of the iris shield is that portion of base sheet 11 which extends between first and second end eyelets 24A and 24B at the ends of the shield. Apertures 26A, 26B extend through the iris shield at the eyelets, extending from the anterior side of the iris shield to the posterior side of the iris shield. Apertures 26A, 26B function as control elements whereby the attending physician can insert a tool into one of the end eyelets thereby to manipulate and otherwise position the ends of the iris shield over the iris during the surgical procedure. Apertures 26A, 26B are located inwardly of ends 16A, 16B, generally equidistant from edge extremities 12, 14 and the respective ends 16A, 16B. Intermediate apertures 26C, 26D, and 26E extend through the main body between the anterior side and the posterior side at intermediate locations along the length of the main body. The attending physician can, if and as desired, insert a tool into any one of apertures 26C, 26D, or 26E thereby to manipulate and otherwise position the respective intermediate portions of the iris shield with respect to the living iris in the eye. The number of apertures can be different from that illustrated, depending on the physical properties and other specifications of the particular iris shield.

As seen in the cross-section of FIG. 5, the main body of the iris shield has a first relatively constant thickness T1 along the length of the main body, including at intermediate apertures 26C, 26D, and 26E. Eyelets 24A, 24B also have relatively constant thicknesses T2, each the same as the other, about the circumferences of the eyelets; the thicknesses T2 of eyelets 24A, 24B, in the embodiments represented by FIGS. 3-5, being greater than thickness T1 of the main body. An exemplary thickness T2 of the eyelets is about 1.7 times the thickness T1 of the main body 22, with a range of about 1.3 times to 2.5 times the thickness T1 of the main body. While the greater thickness of T2 is not limiting, a significant factor in the performance of the iris shield in the anterior chamber, the relatively greater thickness T2 improves the stability of the shield when the shield is being pulled into the injector.

A flange 28 extends from a location at or near inner edge extremity 14 at the posterior side 20, extending posteriorly and toward the outer edge extremity of iris shield 10, typically at an angle of about 30 degrees to about 85 degrees to the surface of posterior side 20 of shield 10. Width "W2" of flange 28 is generally limited to widths which can be projected to intercept the posterior surface of main body 22 at a right angle, reaching the main body within the width "W1", such right angle intercept being illustrated in FIG. 5.

Figure 6:
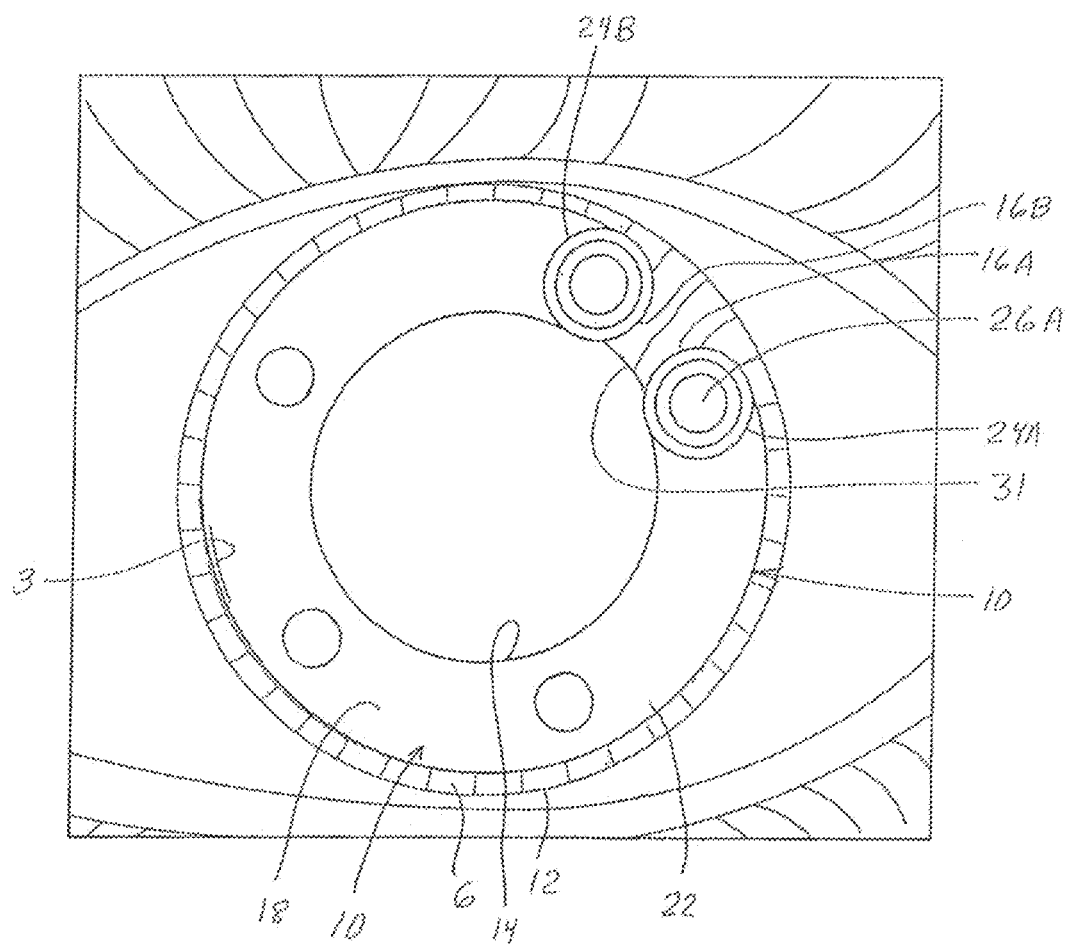
FIG. 6 is a view looking toward the front of an eye from outside the eye, wherein an iris shield as in FIG. 4 has been inserted into the eye through a surgical opening, and the iris shield overlies the iris adjacent the surgical opening.
Figure 7:
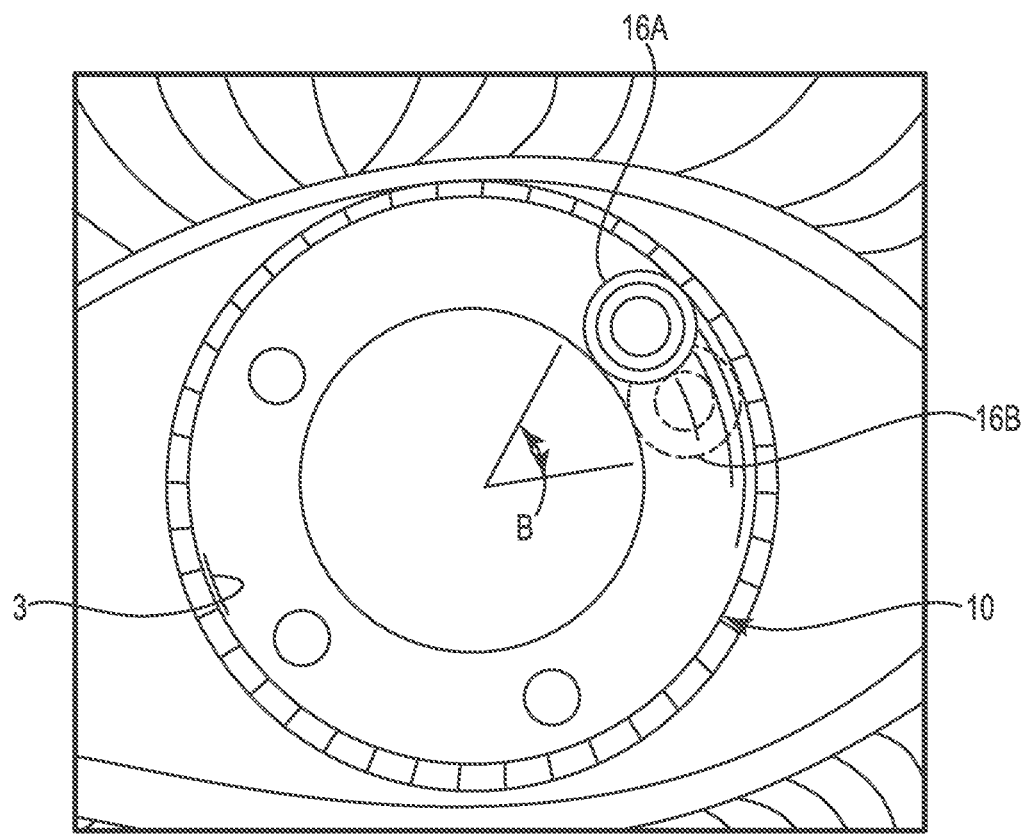
FIG. 7 is a view looking toward the front of an eye as in FIG. 6 wherein a first end portion of the iris shield overlaps a second end portion of the iris shield.

In the embodiments represented by FIGS. 3-5, flange 28 extends, as a single flange, from a location adjacent eyelet 24A, along main body 22, to a location adjacent eyelet 24B. Through substantial experimentation, the inventor has discovered that use of an elongate flange, such as the single flange 28, extending along substantially the full length of main body 22, provides enhanced control of the iris shield while the iris shield is being inserted into the eye and being positioned over the iris. During the positioning of the iris shield in the anterior chamber of the eye, iris shield 10 and/or flange 28 are typically manipulated such that flange 28 is behind, namely posterior of, the living iris in the eye such that the inner edge of the living iris is immobilized in cavity 30 between flange 28 and main body 22 at the inner edge of the main body. A corresponding function of flange 28 is thus to engage the inner edge 31 of the iris in cavity 30, thus to control, immobilize, and otherwise prevent constriction of the iris. Although the iris shield is readily flexed, the polymeric material used in the iris shield has suitable stiffness that the iris shield holds its shape over the iris during the surgery as illustrated in FIGS. 6 and 7, thus generally holding the iris immobile during certain portions of the surgical procedure, respectively preventing the iris from constricting over the pupil of the eye, which would impede visualization of rearwardly-disposed portions of the anterior chamber, where the lens is located, by the attending physician.

Also through substantial experimentation, the inventor has discovered that the iris shield can be predictably inserted into the eye and positioned with the anterior side of the iris shield facing anteriorly and the posterior side facing posteriorly, whereby there is no need to provide a flange on the anterior side of the iris shield. Rather, the anterior side of the iris shield can be flat, without a flange, thus to enhance the surface-to-surface contact between the anterior side of the iris shield and the inner surface of the cornea/sclera adjacent any surgical opening. Accordingly, the anterior side of the main body is preferably devoid of structure corresponding to flange 28.

As a non-limiting example, the thickness T1 of the main body 22 can be about 350 microns and the thickness T2 of the eyelets 24A, 24B can be about 600 microns. Various thicknesses can be specified for the main body and the eyelets depending on the stiffness and resilience of different biocompatible polymeric materials selected for use in making the iris shield. A general range of thicknesses T1, between the anterior surface and the posterior surface, is about 100 microns to about 500 microns, optionally about 200 microns to about 400 microns, yet further optionally about 350 microns.

Thicknesses of the eyelets are about 200 microns to about 1000 microns, optionally about 400 microns to about 800 microns, further optionally about 600 microns.

The thickness of retention flange 28 is about 100 microns to about 350 microns, optionally about 150 microns to about 250 microns, further optionally about 200 microns, with the thickness of the flange typically being less than the thickness of main body 22.

The thickness of main body 22 is driven by a number of factors including, without limitation, the hardness, flexibility, resilience of the material from which the iris shield is made, the width of the iris shield, the flexibility of the main body, foldability of the main body, rigidity of the main body, strength of the main body, and the like. The above physical properties recited for the main body are proxies for the entirety of the iris shield, including flange 28.

FIG. 6 illustrates an iris shield 10 of e.g. FIGS. 3-5 inside an eye 2, the iris shield having been inserted into the eye through surgical opening 3 and laid out over the iris 6, with flange 28 behind the inner edge portion of the iris, using one or more commonly-available ophthalmic surgical tools.

FIG. 7 illustrates an iris shield 10 of e.g. FIGS. 3-5 inside an eye 2, as in FIG. 6 but wherein the length of the iris shield is longer than in FIG. 6 such that the end 16A overlaps, is anterior of, the end 16B. As a result of the overlap, the iris shield covers, overlies the entirety of the circumference of the living iris whereby, contrary to FIG. 6, no portion of the entirety of the length of the iris is unshielded across the full width of the iris. Where the length of the iris shield is such that end 16A overlaps end 16B, the end closest to the iris and surrounding the respective aperture 26A or 268 can optionally have the same thickness "T1" as main body 22 such that both the anterior side and the posterior side of that particular end eyelet are straight line extensions of the main body surfaces on the respective sides of the iris shield.

In the embodiment illustrated in FIGS. 3-5, flange 28 extends from the inner edge extremity of main body 22 at a first angle "α" and at a first flange thickness, and then turns to extend parallel to the posterior surface of the main body and further away from the inner edge extremity at a second thickness greater than the first flange thickness.

Figure 10:
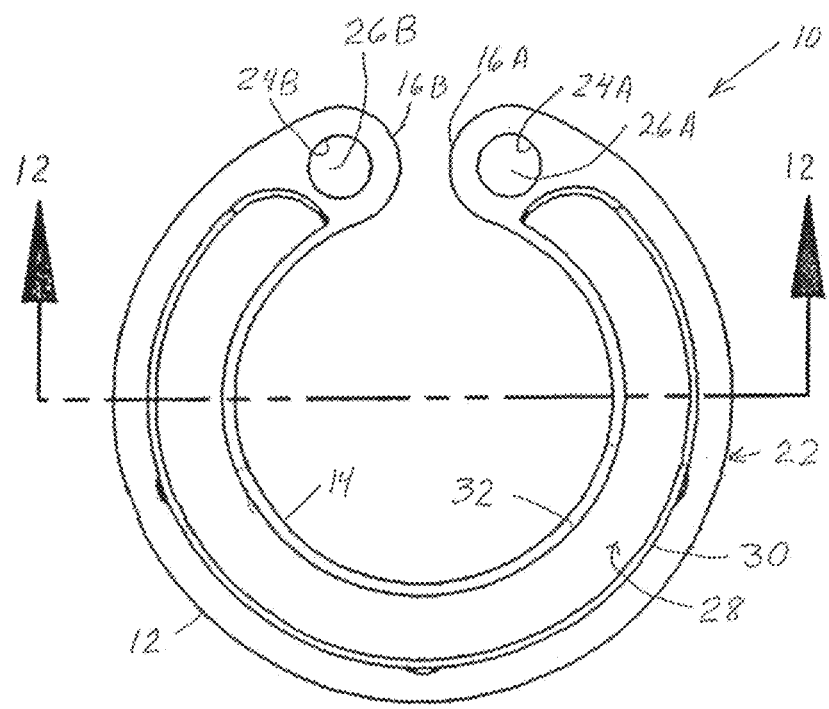
FIG. 10 shows a plan view of the posterior side of a fourth embodiment of iris shields of the invention.
Figure 11:
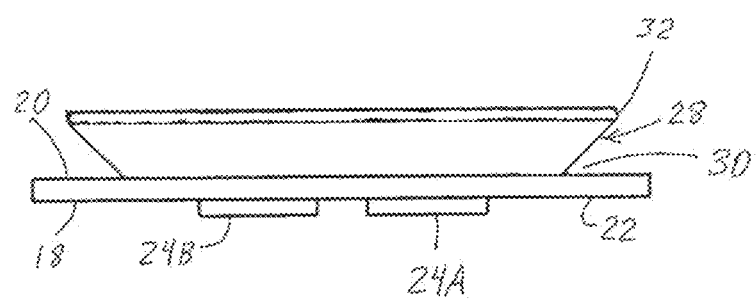
FIG. 11 shows a side elevation view of the iris shield of FIG. 10, wherein the first and second ends of the iris shield are facing away from the viewer and are thus not seen in FIG. 11.
Figure 12:
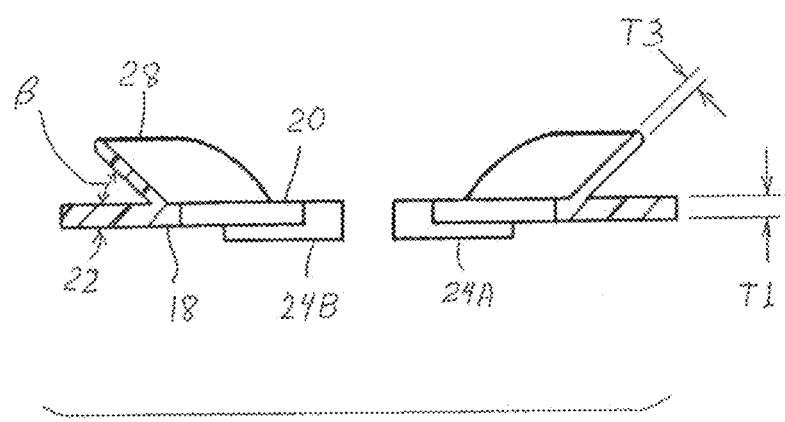
FIG. 12 is a cross-section of the iris shield of FIGS. 10 and 11, taken at 12-12 of FIG. 10.

FIGS. 10-12 illustrate yet another embodiment of iris shields of the invention wherein flange 28 extends from the main body 22 at a constant angle β, which may have the same angular magnitude as angle α, and at a constant thickness "T3" which is less than the thickness "T1" of the main body.

In some embodiments, in iris shields of the invention, first and second ends 16A, 16B extend along at least about 350 degrees of the circumference of the anterior chamber, thereby facilitating the attending physician positioning a portion of the iris shield adjacent each of potentially multiple surgical openings. The length of the iris shield, from the remote edge of end 16A to the remote edge of end 16B can extend any length in e.g. 1 degree increments, to as much as about 410 degrees, about the circumference of the anterior chamber as illustrated at angle B in FIG. 7, and whereby the end portions of the iris shield may overlap each other, including the entirety of the width of the iris shield shielding the full circumference of the iris, as illustrated in FIG. 7. While it is possible for the iris shield to extend greater than 410 degrees, the additional length typically has little or no functional value in a given eye.

Especially where the end portions overlap each other, only a first one of the eyelets need have a thickness T2 greater than the thickness T1 of the main body—whereby the one thicker eyelet can be used in pulling the iris shield into the tubular injector tool, and in pulling the iris shield from the anterior chamber as part of the process of completing the surgical procedure, while the relatively lesser thickness of the second eyelet provides a relatively lesser overall thickness of the shield at a second eyelet. In any of the contemplated uses for iris shield 10, it is completely acceptable for only one of eyelets 24A, 24B to be thicker than main body 22.

The thickness of retention flange 28 is driven by flexibility of the flange, strength of the flange, the ability of the flange to conform to the surface of the iris, and the like under pressure which typically exists in the eye during eye surgical procedures. In general, in fulfilling its functions relative to the iris, inside the anterior chamber, flange 28 has a greater requirement to be foldable, flexible, especially about its locus of attachment to the main body, than any requirement for the main body or the eyelets to be foldable, flexible.

Various preliminary steps may be performed in the surgical procedure of e.g. a cataract removal and lens replacement procedure, prior to any insertion, into the eye, of any material or activity which would increase the internal pressure inside the eye. First a surgical opening is made in the eye, typically in the cornea, anterior of the iris, and laterally displaced from the pupil, thus adjacent, and anterior of, the outer edge of the iris. During the surgical procedure, iris shield 10 is inserted through the surgical opening prior to application of any significant increase in pressure inside the eye enclosure, the iris shield being positioned between the iris and each surgical opening. Thus, iris shield 10 is inserted before any material is injected into the eye or any action is taken to e.g. fracture a crystallized natural lens which is to be removed and replaced.

Typically, the iris shield will be folded on itself lengthwise, e.g. along a longitudinal axis, as the iris shield is being pulled into a tubular injector instrument, such as those used to inject artificial e.g. intraocular lenses into the eye, in order to readily insert the iris shield through the surgical opening. Using a suitable such insertion tool, the iris shield is inserted through the surgical opening, and into the eye. Once the tip of the injector instrument containing the iris shield has passed through the surgical opening, the iris shield, which is inside the instrument, is expelled from the tool and allowed to unfold inside the anterior chamber.

A suitable manipulation tool is then engaged with the iris shield at one or both of apertures 26A, 2613, or any aperture in the main body and used to complete the unfolding of the iris shield if needed, and to position the unfolded iris shield over the iris such that the main body of the unfolded iris shield is disposed, as a generally flat sheet, as shown in e.g. FIGS. 6 and 7, the iris shield generally extending in opposing directions from the surgical opening and about the circumference of the iris. As shown, the sheet is generally flat across the width W1, and it terminates along the inner edge extremity and along the outer edge extremity (refer e.g. to FIGS. 4 and 5). As the iris shield is being positioned in the eye, a portion of the length of the iris shield is positioned adjacent each surgical opening. The iris shield, in its use position and orientation, as illustrated in FIGS. 6 and 7, thus provides a protective covering over the iris at and adjacent each surgical opening, and is generally spaced from the cornea except at the outer edge extremity of the iris where the iris meets the cornea. At that outer edge of the iris, the outer edge of the iris shield is nestled in the cavity created by the outer edge of the iris at the inner surface of the cornea. Where more than one surgical opening is created in the eye, the iris shield is positioned so as to lie adjacent, and on both sides of, and extend along and past, each of the surgical openings.

Any increase in pressure inside the eye is commonly transferred to the iris as an outwardly-directed, anteriorly-directed force, thus urging the full width of the iris, including the inner edge, and the middle of the width, of the iris, to move outwardly of, namely anteriorly of, the eye.

Iris tissue is typically quite soft. Where the iris material is sufficiently soft, the iris tissue can thus flow toward any lower pressure at the surgical opening unless such movement is impeded/blocked. With the iris shield positioned in overlying relationship over the iris as illustrated in FIGS. 6 and 7, such upwardly, and outwardly, anteriorly-directed force urges the full width of the iris against the underside/posterior surface of the iris shield. The iris shield receives that force and spreads the force along the length and width of the iris shield. Since the iris shield has generally-fixed length, width, and height dimensions, and is not liquidous, thus cannot flow, such upwardly, outwardly, anteriorly-directed force moves both the iris and the iris shield, from their rest positions, anteriorly against the outer tissues of the eye, such as against more peripherally-disposed portions of the cornea and optionally against a portion of the sclera.

Thus, while iris shield 10 is quite flexible, and with a portion of the iris shield adjacent each surgical opening 3, the generally limited extensibility of the shield, in the length and width dimensions, does not allow the iris shield to change shape enough to be forced out the surgical opening. And since the iris shield is between the iris and the surgical opening and is wide enough to prevent the iris material from circumventing the iris shield and flowing out the surgical opening, the iris shield serves as an effective barrier, protecting the iris such that iris material does not flow beyond the iris shield toward the surgical opening, and thus does not prolapse out the surgical opening.

With the iris shield in place as shown in FIGS. 6 and 7, the attending physician then continues the surgery according to conventionally-accepted surgical procedures, with instrument elements, supplies, and/or implant elements being passed into and out of the eye enclosure through the one or more surgical openings, and wherein the iris shield is between the iris and the instrument elements, supplies, and/or other implant elements. Thus, the iris shield not only serves to protect the iris from the effects of increases in pressure, the iris shield also serves as a buffer/shield to prevent, or reduce in extent or severity, direct contact of the instruments, supplies, implant elements, and the like, with the rather delicate iris tissue.

Once the pressure inside the anterior chamber of the eye returns to more normal pressures, and where the pressure is expected to not again increase to a high enough level to facilitate prolapse of iris tissue, iris shield 10 is removed through the surgical opening, again using a suitable instrument, e.g. an instrument having a hook on an end thereof, to manipulate the iris shield by interaction with the edges of apertures 26A and/or 26B.

Iris shield 10 can be inserted into the eye any time after a surgical opening is created, with commonly used micro forceps, or with a commonly used injector system wherein the iris shield may be folded lengthwise on itself, e.g. about its longitudinal axis. After the iris shield has been inserted through the surgical opening and into the anterior chamber, forceps or another conventional instrument is engaged in apertures 26A and/or 26B, or other aperture, and thus used to manipulate the iris shield into place over the iris. Once the remaining steps in the surgical procedure have been completed, the iris shield is then removed using a small hook commonly known as a Connor Wand, a Sinskey Hook, or the like.

Once iris shield 10 has been removed from the eye, through one of the surgical openings, the surgery again proceeds and/or concludes according to conventionally-accepted surgical procedures.

While it is desirable that flange 28 extend substantially the full length of main body 22, in some instances, uses, it is desirable that the flange have relatively greater levels of flexibility toward the outer edge 32 than toward the inner edge 34, or relatively greater levels of flexibility toward inner edge 34 than toward outer edge 32 of the flange. To achieve relatively greater flexibility toward the inner edge 34, the thickness of the flange can be less at the inner edge than at the outer edge, as illustrated in FIG. 5, or relief slots, not illustrated, can be provided extending from the inner edge toward the outer edge, but stopping short of the outer edge.

Figure 8:
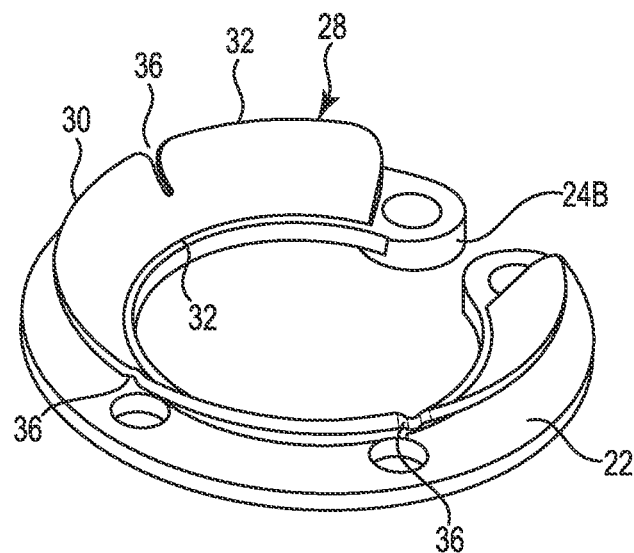
FIG. 8 is a pictorial view as in FIG. 3, showing the posterior side of a second embodiment of iris shields of the invention, wherein relief slots extend inwardly from the outer edge of the single retention flange.

To achieve relatively greater flexibility toward the outer edge 32, the thickness of the flange can be less toward the outer edge than at the inner edge. In the alternative, greater flexibility can be achieved at the outer edge by providing relief slots 36 extending inwardly from the outer edge of flange 28, as illustrated in FIG. 8. Relief slots 36 are designed to provide limited additional flexibility to flange 28 at and adjacent the outer edge of the flange. Relief slots 36 extend from the outer edge of the flange inwardly toward the inner edge of the flange, stopping short of the inner edge. Typically, relief slots 36 extend at least ¼, up to about ⅔, optionally about ½, the distance between the outer edge and the inner edge.

Figure 9:
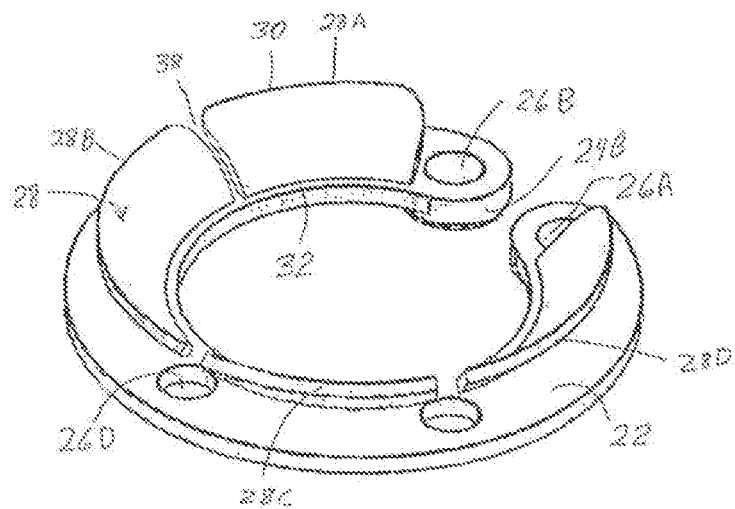
FIG. 9 is a pictorial view as in FIG. 3, showing the posterior side of a third embodiment of iris shields of the invention, the retention flange being defined by multiple elongate flange elements, in place of the single elongate flange element, with limited-length spacings between the flange elements, the multiple elongate flange elements collectively extending substantially the full length of the main body of the iris shield.

In some instances, it is desirable to be able to position flange 28 behind the iris in a series of steps. In such instance, flange 28 can be provided as a plurality of closely-spaced flange elements, illustrated as elements 28A, 288, 28C, 28D in FIG. 9, each extending along a substantial portion, e.g. at least 60 circumferential degrees, of the length of the main body, and each positioned closely adjacent a next adjacent flange element. Namely, the lengths of the spaces 38 between next adjacent flange elements are trivial compared to the lengths of the respective flange elements, whereby the flange elements extend collectively, as singular flange 28, along substantially the full length of the main body. As illustrated in FIGS. 8 and 9, relief slots 36 and spaces 38 may be located adjacent ones of the intermediate apertures thereby to facilitate inserting manipulation tools into the respective intermediate apertures if and as needed.

A given iris shield 10 of the invention, including main body 22, eyelets 24A, 24B, and flange 28, is typically made of a single material composition, and main body 22, eyelets 24A, 24B, and flange 28, in the embodiments illustrated in FIGS. 3-12, are typically fabricated simultaneously as a single piece. A typical fabrication process is injection or other type of molding of a fluid polymeric composition, followed by cooling, and solidification to fix the shield material in the desired configuration.

Iris shields 10 can be made from a variety of polymeric materials, such as various ones of the silicones, acrylics, and collamers. Specific compositions, and combinations of compositions, can be selected by those skilled in the art based on known physical properties, and biocompatibilities of materials of interest. Conventional biocompatible additive packages can be used as desired.

Especially the thickness "T1" of main body 22 is at least in part driven by strength and stiffness of the material of choice once the material is fabricated into the form of the specified main body, eyelets, and flange. Two non-limiting examples of suitable such material for use in iris shields of the invention are NuSil Med-4950 and NuSil Med 4970 silicones, having 50 Shore A and 70 Shore A hardnesses, respectively, both available from NuSil Technology, Carpentaria, Calif. Other conventionally available materials may be selected for other hardness specifications.

Typical hardness of the main body 22 or flange 28, after fabrication, is about 20-75 Shore A, optionally about 20-40 Shore A.

A typical iris shield of the invention, as those shown in FIGS. 3-12, has an outer diameter of about 12 mm to about 13 mm. An iris shield having such outer diameter can be comfortably fitted into, and will generally extend across substantially the entirety of, the anterior chamber of an adult human eye. Opposing sides of the iris shield are generally positioned proximate or against the outer perimeter of the anterior chamber. Given an appropriate stiffness of a single-segment iris shield as in FIGS. 3-12, the iris shield is not easily compressed inwardly toward its own central axis, when inside the anterior chamber, by ambient pressures exerted inside the anterior chamber when the iris shield is being inserted and positioned during the surgical procedure, and opposing sides of the iris shield, across the width of the anterior chamber, tend to center the iris shield about the central axis of the anterior chamber as defined between the front of the eye and the back of the eye. Thus, such single-segment iris shield may inherently and resiliently assist the attending physician in the steps of positioning the iris shield uniformly about the iris such that the iris shield is positioned to cover the portions of the iris adjacent any and all surgical openings, with specific attention to covering as much as possible of the iris tissue which is adjacent any surgical opening. In general, the attending physician positions the iris shield such that, to the extent reasonably possible, the outer edge extremity of the iris shield overlies that portion of the outer edge of the iris which is adjacent a surgical opening, and in addition, as much as possible of the inwardly-directed width of the iris, such that the iris shield overlies that portion of the iris which extends radially from the surgical opening.

Where more than one surgical opening has been created in the eye, the attending physician positions the iris shield so as to so protect the iris adjacent all of the surgical openings.

Prior to beginning a surgical procedure, the surgeon will already know measurements of the patient's eye and will have secured a suitable supply of iris shields of the size or sizes expected to be needed for the specific patient and/or surgical procedure. Such size may be greater than 12-13 mm overall diameter, or may be less than 12-13 mm, depending on the measurements of the respective patient.

Thus, a manufacturer of such iris shields for use in human eyes may typically fabricate such iris shields in at least three outer diameter sizes, for example, the average 12-13 mm size outer diameter, one slightly larger than 12-13 mm, such as 14-15 mm, and one slightly smaller than 12-13 mm, such as 10-11 mm.

The width "W1" of the iris shield, between the outer edge extremity and the inner edge extremity, should be great enough to cover, and provide a shielding effect, to enough of the iris that any portion of the width of the iris which is not overlain by the iris shield is not susceptible to moving to or through the surgical opening. Typical width "W1" of an effective such shield is about 1 mm to about 3 mm, optionally about 2 mm to about 3 mm, optionally about 2.2 mm to about 2.6 mm, optionally about 2.4 mm.

Given the above discussions of the outer diameter of the iris shield and the width of the iris shield, the inner diameter of the iris shield can be calculated to be about 6 mm to about 9 mm, optionally 6 mm to about 7 mm, optionally about 6.2 mm.

The differences between the respective embodiments of iris shield 10 illustrated in FIGS. 3-12 are limited to different flange structures, different overall angular lengths of the iris shield, the number of eyelets, and the number of apertures 26. As shown in at least some of these figures, the retention flange may be generally frustum-shaped.

Figure 13:
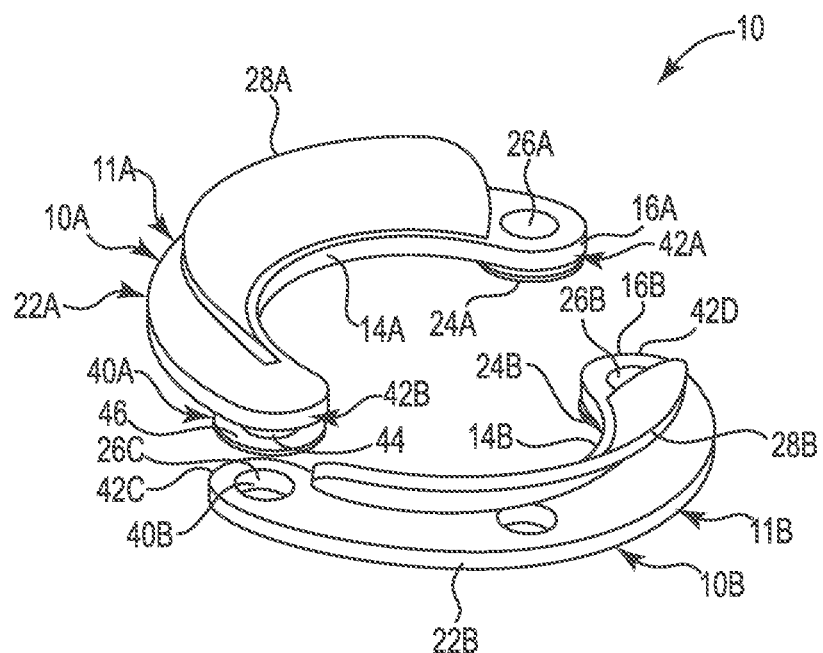
FIG. 13 shows a pictorial representation of a fifth embodiment of iris shields of the invention wherein first and second segments of the iris shield are shown separated from each other, and elements which can form a hinge are in close proximity to each other.
Figure 14:
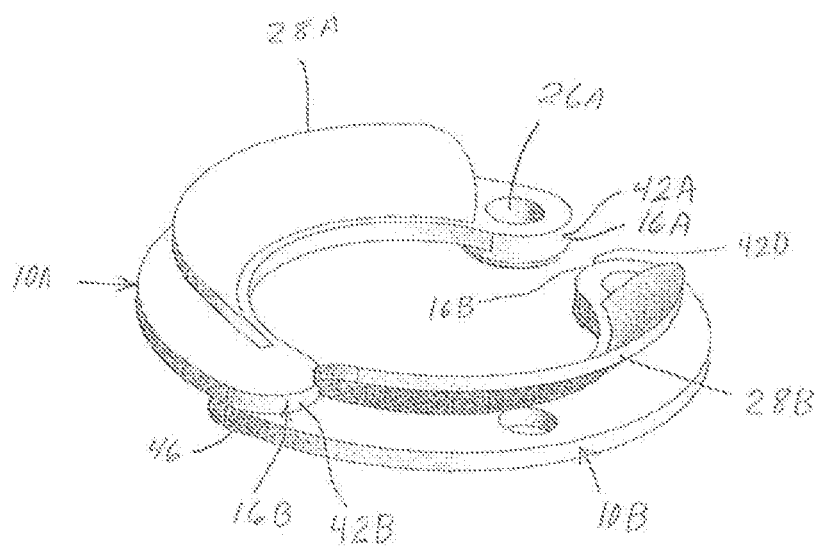
FIG. 14 shows a pictorial representation of the iris shield of FIG. 13 with the first and second iris shield segments assembled to each other at the joined hinge elements, whereby the first and second iris shield segments can pivot with respect to each other about the hinge.

FIGS. 13-14 add the feature of providing the iris shield in multiple shield segments, where each segment represents a portion, but not all, of the angular length of the iris shield between ends 16A and 16B. Each segment, thus, provides a portion, but not all, of base sheet 11, a portion, but not all, of main body 22, and a portion, but not all, of flange 28. In addition, each shield segment includes at least a first hinge element which can be used to hingedly attach the respective shield segment to an adjacent shield segment. At least one of the iris shield segments optionally includes an eyelet 24, surrounding an aperture 26, the eyelet being thicker than that portion of main body 22 which is defined on the same shield segment and proximate an end of the iris shield.

FIGS. 13 and 14 show a such iris shield 10 which includes a first shield segment 10A and a second shield segment 10B. First shield segment 10A has a first base sheet segment 11A, a first shield segment end 42A, and a second shield segment end 42B. As seen in FIG. 14, where shield segments 10A and 10B have been assembled to each other, first segment end 42A is coincident with first end 16A of the assembled iris shield. Eyelet 24A is identified at first segment end 42A. Aperture 26A extends through eyelet 24A at first segment end 42A. Aperture 26B extends through eyelet 24B at fourth segment end 42D. A first main body portion 22A extends from eyelet 24A to second segment end 42B. First flange section 28A extends upwardly and outwardly from a location on the posterior side of base sheet segment 11A, proximate the inner edge extremity 14A of the first main body portion 22A, from a location proximate eyelet 24A, and extends to a location proximate second end 42B.

As in the embodiments of FIGS. 3-12, eyelet 24A at first end 16A is thicker than first main body portion 22A.

Male hinge element 40A is located proximate second segment end 42B of shield element 10A. Male hinge element 40A includes a shaft 44 extending down from base sheet segment 11A proximate second segment end 42B. Circular hinge flange 46 extends outwardly from shaft 44, generally parallel to the anterior side of base sheet segment 11A.

Second shield segment 10B has a second base sheet segment 11B, a third shield segment end 42C, and a fourth shield segment end 42D.

Second flange section 288 extends upwardly and outwardly from a location on the posterior side of base sheet 11B, proximate the inner edge extremity 148 of the second main body portion 22B from a location proximate eyelet 24B, and extends to a location proximate third end 42C. As seen in FIG. 14, wherein shield segments 10A and 10B have been assembled to each other, fourth segment end 42D is coincident with second end 16B of the assembled iris shield 10.

Female hinge element 40B is disposed proximate end 42C of shield element 10B. Female hinge element 40B is defined by an aperture 26C which extends through the base sheet, between the anterior and posterior sides of the iris shield proximate end 42C of second shield segment 10B. Aperture 26C is sized and configured to receive shaft 44 and flange 46 of male hinge element 40A, such that flange 46 extends outwardly from shaft 44 below the anterior side of shield segment 10B, and generally parallel to the anterior side of shield segment 10B. FIG. 14 shows the male and female hinge elements so assembled to each other, thus to assemble the first and second iris shield segments 10A and 10B to each other.

With the hinge elements 40A and 40B so assembled to each other, iris shield segments 10A and 10B can pivot relative to each other about shaft 44 and aperture 26C. Such pivotation facilitates increasing or decreasing the angular orientation of the iris shield segments relative to each other. Such changeable orientation has multiple advantages including (i) facilitating adjusting the overall circumference and/or diameter of the so-assembled iris shield and (ii) facilitating the final positioning of the full length of the iris shield over the living iris during a surgical procedure.

Figure 15:
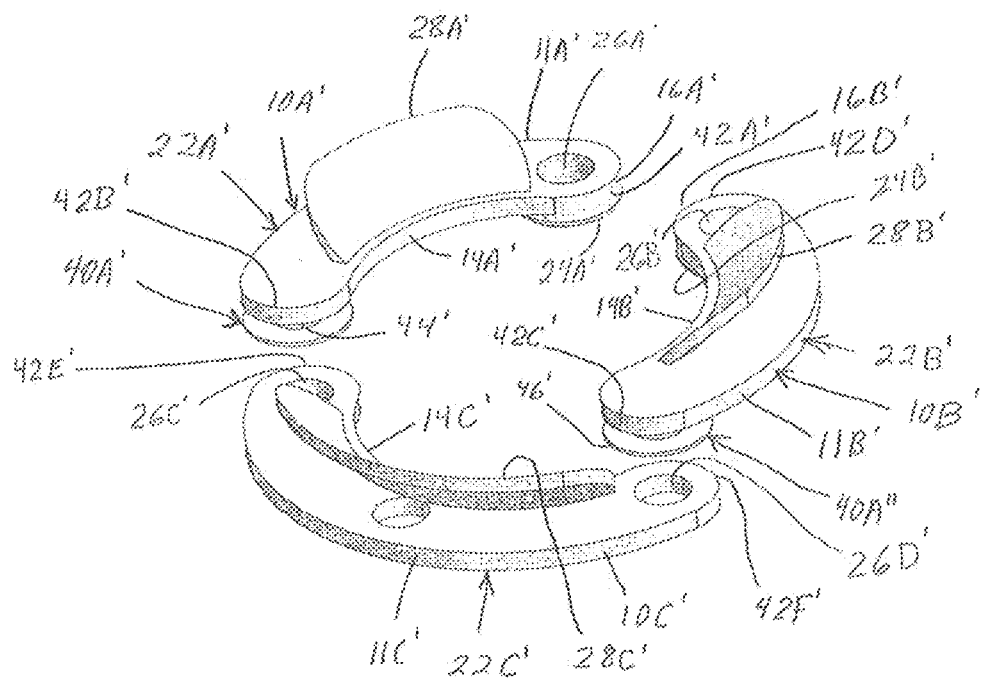
FIGS. 15 and 16 show pictorial representations of a hinged iris shield of the invention as in FIGS. 13 and 14 but wherein first, second, and third iris shield segments are hingedly connected to each other at respective first and second hinges, so as to provide first and second hinge functions.
Figure 16:
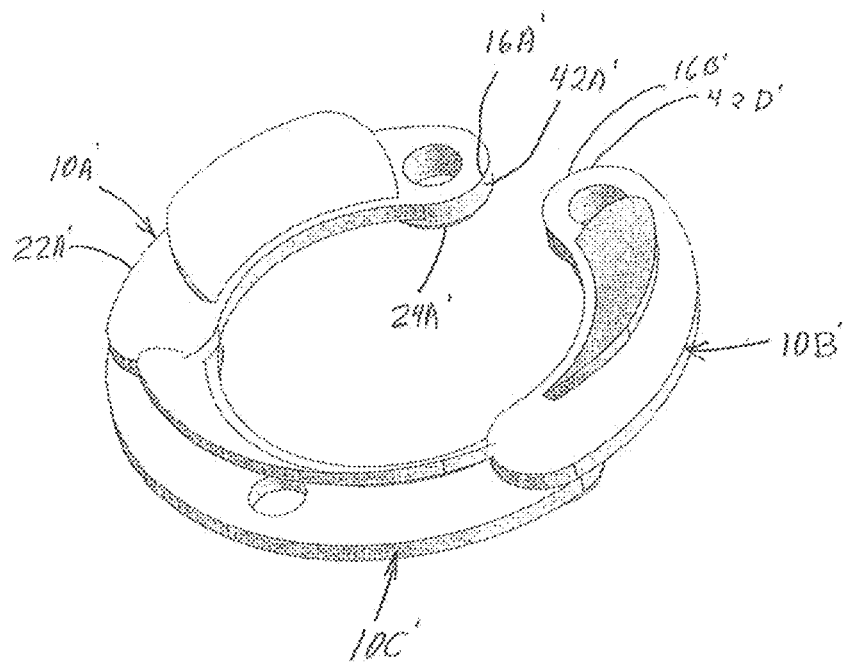

FIGS. 15 and 16 illustrate the same principles as FIGS. 13-14, but using three iris shield segments instead of two iris shield segments. Thus, in FIGS. 15 and 16, iris shield 10 is comprised of a first main body portion 22A' on first iris shield segment 10A', a second main body portion 22B' on second iris shield segment 10B', and a third main body portion 22C' on third iris shield segment 10C'.

A first aperture 26A' extends through first shield segment 22A' at eyelet 24A', at first segment end 42A'. A second aperture 26B' extends through second shield segment 22B' at eyelet 248', at fourth segment end 42D'. Third and fourth apertures 26C' and 26D' extend through third shield segment 22C' at opposing ends 42D' and 42F'.

A first flange section 28A' extends upwardly and outwardly from a location on the posterior side of base sheet segment 11A' proximate inner edge extremity 14A' at first main body portion 22A' from a location proximate eyelet 24A' to a location proximate male hinge element 40A'. A second flange section 28B' extends upwardly and outwardly from a location on the posterior side of base sheet segment 11B' proximate inner edge extremity 14B' at second main body portion 22B' from a location proximate eyelet 24B' to a location proximate male hinge element 40A". A third flange section 28C' extends upwardly and outwardly from a location on the posterior side of base sheet segment 11C' proximate inner edge extremity 14C' at third main body portion 22C' from a location proximate aperture 26C' to a location proximate aperture 26D'. As seen in FIG. 16, where shield segments 10A', 10B', and 10C' have been assembled to each other, first segment end 42A' is coincident with first end 16A' of the assembled iris shield 10 and fourth segment end 42D' is coincident with second end 16B' of the assembled iris shield.

As in the embodiment of FIGS. 13-14, eyelet 24A' at first end 16A' is thicker than first main body portion 22A'.

Male hinge element 40A' on shield segment 10A' and hinge element 40A" on shield segment 10B' are disposed proximate second segment end 42B' on shield element 10A' and third segment end 42C' on shield element 10B'. Each of male hinge elements 40A' and 40A" include a shaft 44' extending down from the respective base sheet segments 11A' and 11B' proximate third and fourth segment ends 42B' and 42C' of first and second shield segments 10A' and 10B'. Circular hinge flanges 46' extend outwardly from shafts 44', generally parallel to the anterior sides of base sheets 11A' and 11B'.

First and second female hinge elements 40B' are disposed proximate opposing ends 42E' and 42F' of shield element 10C'. Female hinge elements 40B' are defined by apertures 26C' and 26D'. Apertures 26C' and 26D' are sized and configured to receive shafts 44' and flanges 46' of the male hinge elements, such that flanges 46' extend outwardly from shafts 44' below the anterior side of shield segment 10C', and generally parallel to the anterior side of shield segment 10C'. FIG. 16 shows the male and female hinge elements so assembled to each other, thus to assemble the first, second, and third iris shield segments 10A' 10B', and 10C' to each other.

With the hinge elements so assembled to each other, iris shield segments 10A', 10B', and 10C' can pivot relative to each other about shafts 44' and apertures 26C' and 26D'.

The choice of whether to use an iris shield of e.g. FIGS. 3-12 having a single flange 28, or an iris shield of FIGS. 13-16 having multiple iris shield segments embodying multiple flange segments is a judgment decision regarding the value of a single flange versus greater rotational flexibility between or among iris shield segments. The single flange 28 embodied in the embodiments of FIGS. 3-12 is simpler and may thus be easier to manipulate inside the anterior chamber. The multiple flange embodiments of FIGS. 13-16, though more complex, can be fitted into and within a greater variety of eye sizes, whereby the attending physician can select a multiple flange iris shield with greater confidence that the selected iris shield will fit into the eye of a given patient.

An iris shield of the invention is used only during the surgical procedure. The iris shield is removed as one of the latter steps in the surgical procedure. Namely, the iris shield does not remain in the eye at the completion of the surgical procedure.

While the invention has been described above with respect to use in a human eye, the iris shields disclosed herein can as well be used in animal eyes. For such uses, the inner diameter, the outer diameter, and the width of the iris shield will be specified and fabricated according to the sizes of the eyes to be treated.

While the invention has been described in conjunction with the specific embodiments outlined above, many alternatives, modifications and variations will be apparent to those skilled in the art. Accordingly, the embodiments of the invention, as set forth above, are intended to be illustrative, not limiting. Various changes may be made without departing from the spirit and scope of this invention.

What is claimed is:

1. An iris shield for insertion through a surgical opening and into an anterior chamber of an eye during a surgery, the anterior chamber having a circumference, the eye comprising an iris in the anterior chamber, the iris having an outer edge, an inner edge, and an iris width between the iris outer edge and the iris inner edge, the iris shield comprising:
   a flexible biocompatible polymeric sheet, the sheet, and correspondingly the iris shield, having an anterior side for facing forwardly in the eye, and a posterior side for facing rearwardly in the eye, an inner edge extremity and an outer edge extremity, and a width (W1) between the inner edge extremity and the outer edge extremity; and
   a retention flange extending from the biocompatible polymeric sheet adjacent the inner edge extremity, the retention flange being disposed on the posterior side of the biocompatible polymeric sheet,
   wherein the sheet is generally flat across the width W1, and terminates along the inner edge extremity and along the outer edge extremity,
   wherein the sheet has first and second ends, and a first manipulation aperture proximate the first end and a second manipulation aperture proximate the second end, the first and second manipulation apertures extending through the sheet from the anterior side to the posterior side, the sheet further including a first eyelet substantially surrounding the first manipulation aperture, the sheet and the first eyelet having a respective sheet thickness and eyelet thickness along a direction from the anterior side to the posterior side, the eyelet thickness being greater than the sheet thickness;
   wherein the retention flange is generally frustum-shaped, and configured to extend along at least 60 degrees of the circumference of the anterior chamber; and
   wherein the iris shield includes no additional retention flanges on the posterior side of the sheet other than the retention flange.

2. The iris shield of claim 1, the retention flange configured to extend along at least about 235 degrees of the circumference of the anterior chamber.

3. The iris shield of claim 2, the retention flange configured to extend along at least about 305 degrees of the circumference of the anterior chamber.

4. The iris shield of claim 1, wherein the first and second ends of the sheet overlap each other.

5. The iris shield of claim 1, wherein the first eyelet has a first side corresponding to the anterior side of the sheet, and a second side corresponding to the posterior side of the sheet, the second side comprising a straight line extension of a main body portion of the sheet.

6. The iris shield of claim 1, wherein a ratio of the eyelet thickness to the sheet thickness is in a range from 1.3 to 2.5.

7. The iris shield of claim 1, wherein the iris shield is adapted for insertion into the eye through an injector, and the increased thickness of the first eyelet relative to the sheet improves a stability of the iris shield when pulled into the plunger.

8. The iris shield of claim 1, wherein sheet, the retention flange, and the first eyelet are made of a single material composition.

9. The iris shield of claim 1, wherein the retention flange extends along substantially a full length of the sheet from the first end to the second end.

10. The iris shield of claim 1, wherein the retention flange has an outer edge and an inner edge, and a thickness of the retention flange is less toward the outer edge than at the inner edge.

11. The iris shield of claim 1, the sheet further including a second eyelet substantially surrounding the second manipulation aperture.

12. The iris shield of claim 11, wherein the retention flange extends as a single flange from a first location proximate the first eyelet to a second location proximate the second eyelet.

13. The iris shield of claim 11, wherein the second eyelet has a second eyelet thickness that is not greater than the sheet thickness.

14. The iris shield of claim 1, wherein the second eyelet has a second eyelet thickness that is greater than the sheet thickness.

15. An iris shield for insertion through a surgical opening and into an anterior chamber of an eye during a surgery, the anterior chamber having a circumference, the eye comprising an iris in the anterior chamber, the iris having an outer edge, an inner edge, and an iris width between the iris outer edge and the iris inner edge, the iris shield comprising:
   a flexible biocompatible polymeric sheet, the sheet, and correspondingly the iris shield, having an anterior side for facing forwardly in the eye, and a posterior side for facing rearwardly in the eye, an inner edge extremity and an outer edge extremity, and a width (W1) between the inner edge extremity and the outer edge extremity; and
   a retention flange extending from the biocompatible polymeric sheet adjacent the inner edge extremity, the retention flange being disposed on the posterior side of the biocompatible polymeric sheet,
   wherein the sheet is generally flat across the width W1, and terminates along the inner edge extremity and along the outer edge extremity,
   wherein the sheet has first and second ends, and a first manipulation aperture proximate the first end and a second manipulation aperture proximate the second end, the first and second manipulation apertures extending through the sheet from the anterior side to the posterior side, the sheet further including a first eyelet substantially surrounding the first manipulation aperture and a second eyelet substantially surrounding the second manipulation aperture, the sheet and the first eyelet having a respective sheet thickness and eyelet thickness along a direction from the anterior side to the posterior side, the eyelet thickness being greater than the sheet thickness; and wherein the retention flange is generally frustum-shaped and extends as a single flange from a first location proximate the first eyelet to a second location proximate the second eyelet.

16. The iris shield of claim 15, wherein the first and second ends of the sheet overlap each other.

17. The iris shield of claim 15, wherein the first and second ends of the sheet do not overlap each other.

18. The iris shield of claim 15, wherein sheet, the retention flange, and the first and second eyelets are made of a single material composition.

19. The iris shield of claim 15, wherein the second eyelet has a second eyelet thickness that is not greater than the sheet thickness.

20. The iris shield of claim 15, wherein the second eyelet has a second eyelet thickness that is greater than the sheet thickness.

21. The iris shield of claim 15, wherein the iris shield is adapted for insertion into the eye through an injector, and the increased thickness of the first eyelet relative to the sheet improves a stability of the iris shield when pulled into the plunger.

* * * * *